US009795143B2

United States Patent
Escobar Valdes et al.

(10) Patent No.: US 9,795,143 B2
(45) Date of Patent: Oct. 24, 2017

(54) COMPOSITION FOR OBTAINING BIOLOGICAL INSECTICIDE COMPRISING STRAINS OF BACILLUS THURINGIENSIS

(71) Applicant: BIO INSUMOS NATIVA LTDA., Talca (CL)

(72) Inventors: Paulo Andres Escobar Valdes, Talca (CL); Eduardo Patricio Donoso Cuevas, Talca (CL); Gustavo Adolfo Lobos Prats, Talca (CL)

(73) Assignee: BIO INSUMOS NATIVA S.p.A., Talca (CL)

( * ) Notice: Subject to any disclaimer, the term of this patent is extended or adjusted under 35 U.S.C. 154(b) by 0 days.

(21) Appl. No.: 14/351,467

(22) PCT Filed: Oct. 16, 2012

(86) PCT No.: PCT/CL2012/000060
§ 371 (c)(1),
(2) Date: Jul. 3, 2014

(87) PCT Pub. No.: WO2013/053068
PCT Pub. Date: Apr. 18, 2013

(65) Prior Publication Data
US 2014/0328817 A1 Nov. 6, 2014

(30) Foreign Application Priority Data
Oct. 13, 2011 (CL) .................................. 2542-2011

(51) Int. Cl.
*A01N 63/02* (2006.01)
*A01N 63/00* (2006.01)
(52) U.S. Cl.
CPC .................................. *A01N 63/00* (2013.01)
(58) Field of Classification Search
None
See application file for complete search history.

(56) References Cited

U.S. PATENT DOCUMENTS

| | | | |
|---|---|---|---|
| 4,902,507 A | | 2/1990 | Morris et al. |
| 5,403,809 A | * | 4/1995 | Miller ...................... B01J 21/18 |
| | | | 502/413 |
| 5,516,514 A | * | 5/1996 | Iizuka et al. .................. 424/115 |

FOREIGN PATENT DOCUMENTS

| | | |
|---|---|---|
| EP | 0448070 A1 | 3/1991 |
| KR | 20050018767 A | 2/2005 |
| KR | 20100103199 A | 9/2010 |

OTHER PUBLICATIONS

US Geological Survey, Mineral Commodity Summaries, 186-187, 2011.*
Shahini, Shpend, Kullaj, Endrit, Ç akalli, Adriatik, Ç akalli, Majlinda, Lazarevska, Stanislava, Pfeiffer, Douglass G. and Gumeni, Fatmir(2010) 'Population dynamics and biological control of European grapevine moth (Lobesia botrana: Lepidoptera: Tortricidae) in Albania using different strains of Bacillus thuringiensis', International Journal of Pest Management, 56: 3, 281-286.
Inigo Ruiz De Escudero, Anna Estela, Baltasar Escriche and Primitivo Caballero, "Potential of the Bacillus thuringiensis Toxin Reservoir for the Control of Lobesia botrana (Lepidoptera: Tortricidae), a Major Pest of Grape Plants", Applied and Environmental Microbiology, Jan. 2007, p. 337-340.
Marcela Vasquez, Carolina Parra, Elizabeth Hubert, Patricio Espinoza, Cristina Theoduloz and Luis Meza-Basso, "Specificity and Insecticidal Activity of Chilean Strains of Bacillus thuringiensis",Journal of Invertebrate Pathology, vol. 66, 1995, p. 143-148.
A. A. Ifoulis and M. Savopoulou-Soultani, "Biological Control of Lobesia botrana (Lepidoptera: Tortricidae) Larvae by Using Different Formulations of Bacillus thuringiensis in 11 Vine Cultivars Under Field Conditions", Journal of Economic Entomology, 97(2): 340-343.
C. Ioriatti, G. Anfora, M. Tasin, A. De Cristofaro, P. Witzgall and A. Lucchi, "Chemical Ecology and Management of Lobesia botrana (Lepidoptera: Tortricidae)", J. Econ. Entonmol. 104(4): 1125-1137 (2011).
Lorena Niedmann Lolas and Luis Meza-Basso, "Evaluation of Native Strains of Bacillus thuringiensis as an Alternative of Integrated Management of the Tomato Leaf Miner (Tuta absoluta Meyrick; Lepidoptera: Gelechiidae) in Chile", Agricultura Tecnica (Chile), 66(3): 235-246 (Jul.-Sep. 2006).

* cited by examiner

*Primary Examiner* — David Berke-Schlessel
(74) *Attorney, Agent, or Firm* — Eric Alspaugh; TechLaw LLP

(57) ABSTRACT

The invention refers to formulae for biologic control of insect plagues in plants, free of chemicals, that include deposited *Bacillus thuringiensis* var. kurstaki strains, as well as crystals from endotoxins derived from said strains. It also refers to the biologic control method for the protection of plants from insect plagues through the application of the said formula on plants, their parts, the soil, or their surroundings.

14 Claims, 4 Drawing Sheets

Damaged bunches (light)

T2 BI (3 strains)

Damage % (leaflets)

BI (3 strains)    Chemical

Treatments

Larvae / plant

BI (3 strains)   Chemical

Treatments

Bunches / plant

BI (3 strains)   Chemical

Treatments

% mortality

Control          BI (3 strains)          Engeo

COMPOSITION FOR OBTAINING BIOLOGICAL INSECTICIDE COMPRISING STRAINS OF BACILLUS THURINGIENSIS

This application is the National Stage of International Application PCT/CL2012/000060, filed Oct. 16, 2012, which claims priority to Chilean patent application CL 2542-2011, filed Oct. 13, 2011.

DESCRIPTIVE REPORT

The invention refers to an insecticide composition with a wide action spectrum on insects that are plague, mainly Lepidoptera, such as *Tuta absoluta, Proeulia* spp., *Spodoptera frugiperda, Plutella xylostela, Agrotis* spp, *Lobesia botrana*, among other, for which formulae are used that include at least one strain selected from the group formed by *Bacillus thuringiensis* var. kurstaki (Bt) strains, NRRL B-50551, deposited by BIO INSUMOS NATIVA LTDA. Parcelo Antilhue Lole 432, Ruta 5 Km 2645, Mauk, Chile, with the Agricultural Research Culture Collection (NRRL) International Depositary Authority, 1815 North University Street, Peoria, Ill. 61604 U.S.A., on Aug. 22, 2011, for which the viability test was performed on Aug. 29, 2011 by the International Depository Authority and this deposit is capable of reproduction, deposit number NRRL B-50552, deposited by BIO INSUMOS NATIVA LTDA. Parcelo Antilhue Lole 432, Ruta 5 Km 2645, Mauk, Chile, with the Agricultural Research Culture Collection (NRRL) International Depositary Authority, 1815 North University Street, Peoria, Ill. 61604 U.S.A., on Aug. 22, 2011, for which the viability test was performed on Aug. 29, 2011 by the International Depository Authority and this deposit is capable of reproduction, and deposit number NRRL B-50553, deposited by BIO INSUMOS NATIVA LTDA. Parcelo Antilhue Lole 432, Ruta 5 Km 2645, Mauk, Chile, with the Agricultural Research Culture Collection (NRRL) International Depositary Authority, 1815 North University Street, Peoria, Ill. 61604 U.S.A., on Aug. 22, 2011, for which the viability test was performed on Aug. 29, 2011 by the International Depository Authority and this deposit is capable of reproduction. Hereinafter, these strains shall be called NRRLB-50551, NRRLB-50552, and NRRL B-50553, respectively.

Many of these plagues have been successfully controlled at world level by applying different insecticides and by using sexual confusion (Ioratti et al., 2011); however, restrictions in the registration and tolerance of some of the said insecticides which, in general, contain chemical products, make it necessary to assess new insecticides of biologic origin as alternatives for a comprehensive handling of this plague.

Micro-biologic insecticide Betk-03 corresponds to a formula containing a Bt strain or a mixture of two or three Bt strains for the control of some Lepidoptera plague (Vásquez et al., 1995; Niedmann & Meza-Basso, 2006), which could affect grape berry moth and be included as an alternative for the handling of this plague.

This formula is characterized, in addition to the above mentioned strains, for including toxins in the form of crystals, as well as viable bacteria spores and other products from bacteria fermentation, jointly or isolated.

Formulae may be in the form of a capsule to prepare a suspension, a bait, a combipack, concentrates, emulsifiables, an encapsulated or miscible concentrate, or ultra-low volume suspension; ultra-low volume tablets; oil emulsions in water, water in oil for seed treatment; concentrate gel or paste, emulsifiable gel, gel for seed treatment; emulsifiable granules, encapsulated, fine, soluble, and dispersible; macro granules, micro granules; paste; contact, wettable, and dispersible powder for seed treatment; solution for seed treatment, concentrate suspension for seed treatment, without excluding other, and including all the formulae above described in any of their conventional forms. They may be used as carriers, without excluding other argyle, kaolin, talc, zeolite, water, vegetable oils, paraffinic and non paraffinic minerals, among other agents.

The invention composition allows controlling plagues without the use of conventional insecticides and, due to its characteristics, it does not present environmental restrictions, with the advantage of being used in organic production or other certification systems, or even applied immediately before the harvest.

With regard to the state of the art, we may mention patent ES 2 057 638, which refers to an insecticide composition including:
 (a) *Bacillus thuringiensis* biomass or only its toxin, and
 (b) One or more phospholipids or a substance with high phospholipids content.

The said reference protects a weighted ratio (a) computed as dry substance in front of (b), included in the range from 1:0.2 to 1:5, containing at least one anionic surfactant selected from fatty acids esters ($C_{10}$-$C_{20}$) with optionally ethoxylated glycerol or sorbitol. It describes a composition where the *Bacillus thuringiensis* biomass weighted ratio or its toxin regarding the said surfactants is included in the 10.2 to 1:5 range. It also states that the said *Bacillus thuringiensis* strains are selected from the donegani, kurstaki, san diego, and tenebrionis varieties. It also mentions that phospholipids are selected from phosphatidylcholine, phosphatidylethanolamine, phosphatidylinositol, phosphatidylglycerol and its hydrogenated, hydroxyl and ethoxylated derivatives, indicating that the substance with high phospholipids contents is soy lecithin or its derivatives.

The purpose of this invention is to provide a biologic insecticide composition for plague control in agricultural, forestry, ornamental, domestic use, and wild plants, especially plagues such as tomato moth (*Tuta absoluta*), brassica moth (*Plutella xylostella*), Proeulia (*Proeulia* spp), cutworms (*Agrotis* spp.), alfalfa looper (*Spodoptera frugiperda*), and grape berry moth (*Lobesia botrana*) among other plagues.

The composition is formed by at least one strain selected from the group formed by NRRL B-50551, NRRL B-50552, and NRRL B-50553 strains, as well as from their possible combinations.

In one form, the composition is formed by at least two strains selected from the group formed by NRRL B-50551, NRRL B-50552, and NRRL B-50553, as well as from their possible combinations.

In an additional form, the composition is formed by a combination of NRRL B-50551, NRRL B-50552, and NRRL B-50553 strains. In another aspect, the invention also includes toxin crystals produced by NRRL B-50551, NRRL B-50552, and NRRL B-50553 strains.

In the present invention, bacteria insecticide (BI) NRRL B-50551, NRRL B-50552, and NRRL B-50553, their possible combinations, and the formulae they contain, allow controlling plagues without the use of conventional insecticides which, due to their characteristics, do not present environmental restrictions, being possible to use them in conventional or organic production, or in another certification system.

BRIEF DESCRIPTION OF FIGURES

The following figures provide general information on the results demonstrated and incidence obtained with the use or application on plants cultivated with the use or application of formulae prepared with the different combinations of bacteria strains NRRL B-50551, NRRL B-50552, and NRRL B-50553; the said figures are an integral part of the invention.

DESCRIPTION OF THE INVENTION

Figure 1:
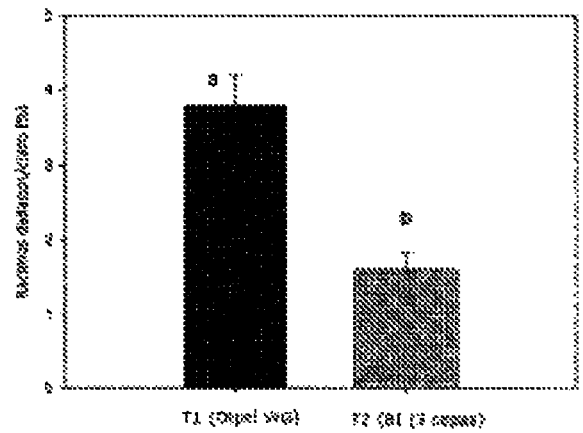
FIG. 1 shows a diagram with the percentage of bunches damaged by *Proeulia* in orchard handling (reference insecticide) and by *B. thuringiensis* (BI); bars indicated a standard error. Different letters show significant differences between treatments (Tukey p<0.05).
Figure 2:
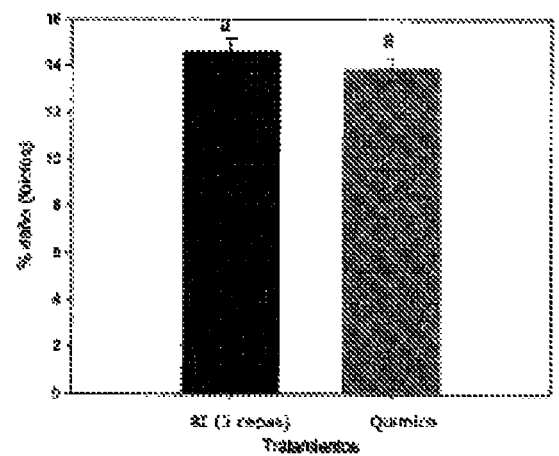
FIG. 2 shows a diagram with the reference chemical insecticide effect and that of BI on the percentage of damage on tomato leaflet attacked by *Tuta absoluta*.
Figure 3:
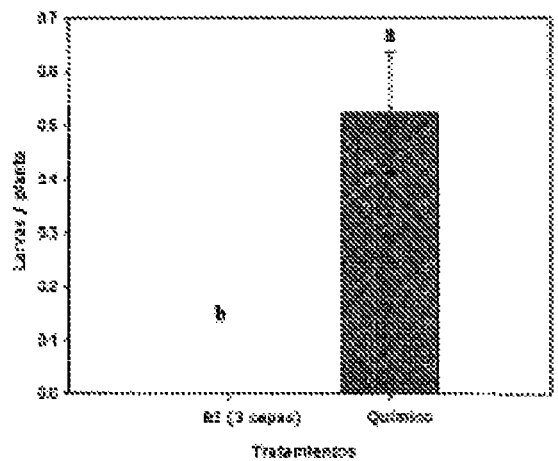
FIG. 3 shows a diagram with the reference chemical insecticide effect, and that of BI on the number of *Tuta absoluta* live larvae on tomato plants.
Figure 4:
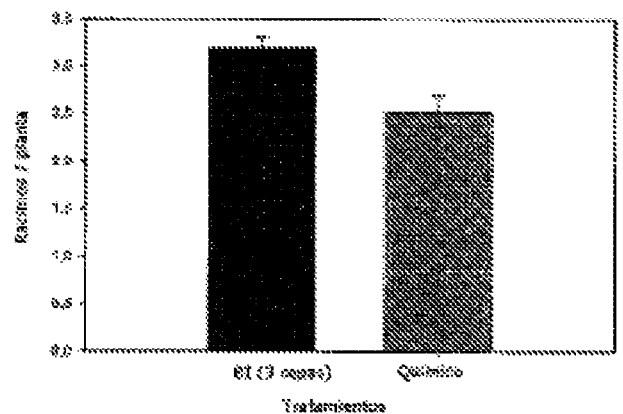
FIG. 4 shows a diagram with the BI application effect on the number of bunches per tomato plant attacked by *Tuta absoluta*.
Figure 5:
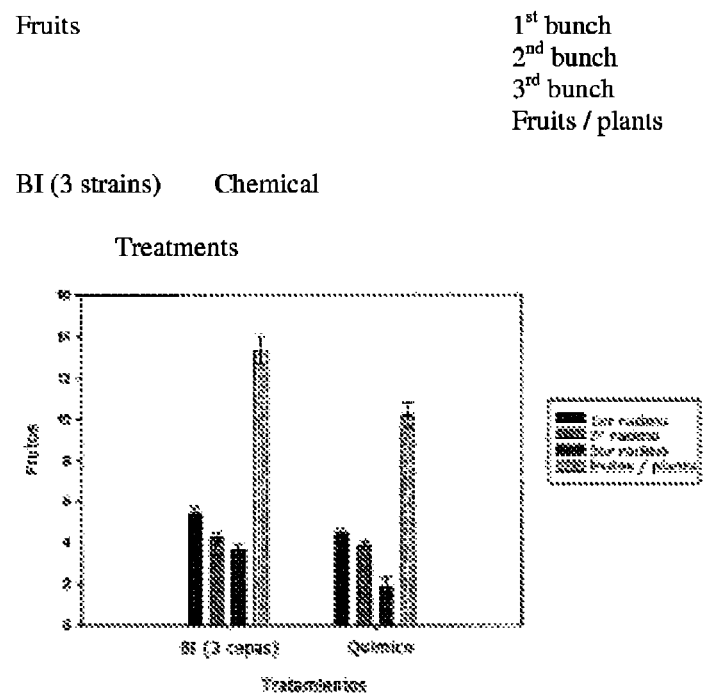
FIG. 5 shows a diagram with the BI application effect on the number of fruits, per bunch and total, on tomato plants attacked by *Tuta absoluta*.
Figure 6:
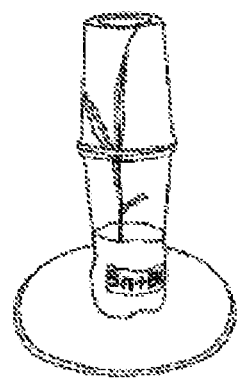
FIG. 6 shows the BI effect on *Agrotis* spp. larvae mortality in maize plants.
Figure 7:
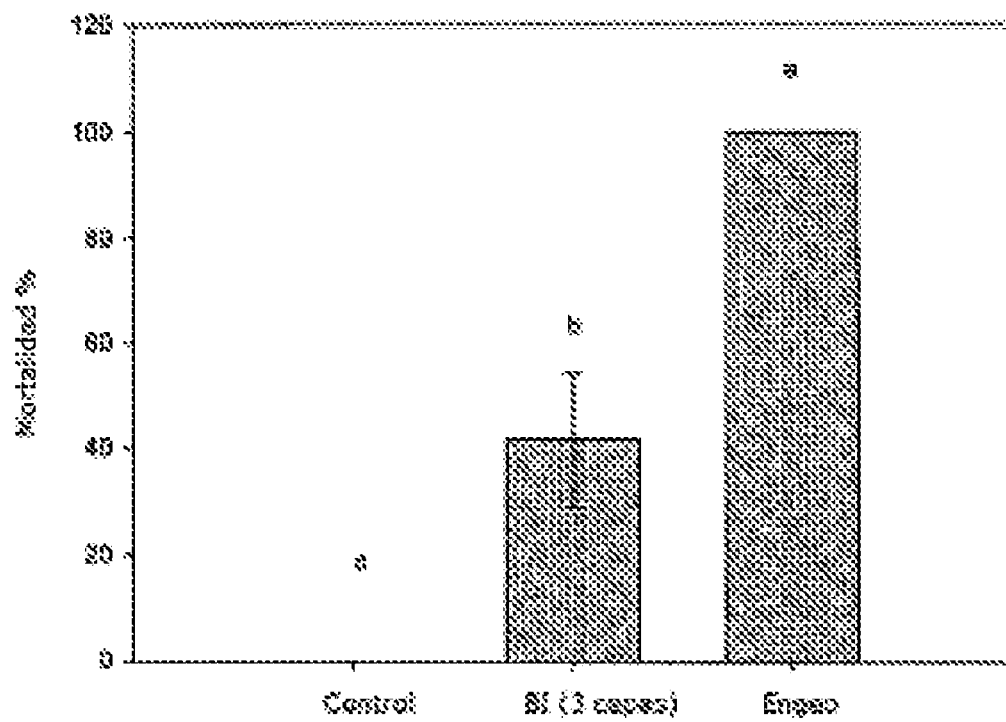
FIG. 7 shows the BI effect on *agrotis* larvae mortality compared to a chemical and a control insecticide.

This invention refers to an insecticide composition with a wide action spectrum on insects that are plagues, mainly Lepidoptera, among which we may find: *Tuta absoluta, Proeulia* spp., *Spodoptera frugiperda, Plutella xylostela, Agrotis* spp, and *Lobesia botrana*, among other. For the composition, formulae were used that include at least one strain selected from the group formed by *Bacillus thuringiensis* var. kurstaki strains and NRRL B-50551, NRRL B-50552, and NRRL B-50553 strains. For this reason, the invention composition is based on the use, without difference, of the said strains, their mixtures, as well as their toxins, which may include forms such as a suspension capsule for the treatment of seeds or a bait in any of its forms, a combi pack in any of its forms, such as a concentrate, encapsulated, miscible, and ultra-low volume; tablets in any of their forms or in the form of ultra-low volume, such as oil-in-water or water-in-oil emulsions for the treatment of seeds in the form of gel or concentrate paste, emulsifiable gel, and gel for the treatment of seeds; in the form or dispersible, encapsulated, fine, soluble, and emulsifiable granules; in the form of macro and micro granules; in the form of paste; in the form of contact, wettable, and dispersible powder in the treatment of seeds; in the form of a solution for seed treatment, without excluding other possible forms applicable in the technical area of this application. The formula can optionally include carriers for the said micro-organisms, such as clay, kaolin, talcum, zeolite, water, vegetable oils, and paraffinic or non-paraffinic minerals, without excluding other agents, to carry the invention *Bacillus thuringiensis* var. kurstaki strains NRRL B-50551, NRRL B-50552, and NRRL B-50553, which are added to the formula in concentrations in a range from 10 to $10^{10}$ spores/g; preferably from $10^5$ to $10^{10}$ UFC/g.

The invention refers to an insecticide composition with a wide action spectrum on insects that are plagues, preferably those of the Lepidoptera kind, among which we may find: *Tuta absoluta, Proeulia* spp., *Spodoptera frugiperda, Plutella xylostel, Agrotis* spp. *Lobesia botrana*, among other, for which formulae are used that include at least one strain selected from the group formed by *Bacillus thuringiensis* var. kurstaki strains NRRL B-50551 NRRL B-50552, and NRRL B-50553. This formula is characterized by the inclusion, in addition to those mentioned above, of a formula that uses toxins in the form of crystal, as well as viable bacteria spores and other products from bacteria fermentation, jointly or individually.

DETAILED DESCRIPTION OF THE INVENTION PREFERRED MODES

Definitions

The following terms and expressions are used along this description, and are known and understood by any expert in the technology.

The term "block", as used in this description, refers to a cultivation area with homogeneous management.

The expression "degree days", as used in this description, refers to temperature accumulation, according to the difference between average temperature and threshold temperature for plague development.

The expression "application threshold", as used in this description, refers to the size of the population requiring handling in order to avoid crop damage.

The expression "real leaves", as used in this description, refers to the leaf formed by leaflets.

In one mode, the invention refers to a formula for biologic control of insect plagues on plants, free of chemicals, where the said formula includes at least two strains of *Bacillus thuringiensis* var. kurstaki selected from the group formed by strains NRRL B-50551, NRRL B-50552, and NRRL B-50553, deposited at ARS-USDA, as well as crystals of endotoxins derived from the said strains.

In another mode, the invention refers to a formula for biologic control of insect plagues on plants, free of chemicals, where the said formula includes the three strains of *Bacillus thuringiensis* var. kurstaki, NRRL B-50551, NRRL B-50552, and NRRL B-50553, as well as crystals of endotoxins derived from the said strains.

In an additional mode, the invention refers to a formula for biologic control of insect plagues on plants, free of chemicals, where the said formula includes at least one strain of *Bacillus thuringiensis* var. kurstaki selected from the group formed by strains NRRL B-50551, NRRL B-50552, and NRRL B-50553, as well as crystals of endotoxins derived from the said strains.

In another mode, the invention refers to a formula for biologic control of insect plagues on plants, free of chemicals, found in a form selected from the group and formed by capsule in suspension for seed treatment; a bait in any of its forms; a combi pack in any of its forms, concentrates, emulsifiables; concentrate, encapsulate, miscible, and ultra-low volume suspensions; tablets in any of their forms, of ultra-low volume; oil-in-water and water-in-oil emulsions in gel or concentrate paste form, and emulsifiable gel; dispersible, encapsulated, fine, soluble, and emulsifiable granules; macro or micro granules; paste; contact, wettable, and dispersible powder; a solution, and a concentrate suspension, among other.

In an additional mode, the invention refers to a formula for biologic control of insect plagues on plants, free of chemicals, where the formula also includes carriers selected from the group formed by clay, kaolin, talcum, zeolite, water, vegetable oils, and paraffinic or non-paraffinic minerals.

In an additional mode, the invention refers to a formula for biologic control of insect plagues on plants, free of chemicals, which includes concentrations from $10^2$ UFC/g to $10^{12}$ UFC/g UU of strains NRRL B-50551, NRRL B-50552, and NRRL B-50553 or from their combinations.

In one mode, the invention refers to a formula for biologic control to protect plants from insect plagues, where the method is the application of a formula, according to some of the above-described modes, to plants, their parts, soil, or surroundings.

A preferred mode of the invention considers the application of the formula for biologic control of insect plagues on plants, free of chemicals, as a biologic control method where the formula is applied on plants and/or their parts, selected from flowers, fruits, seeds, leaves, stems, roots, and rhizomes, among other; protecting plants from pathogen insect attacks. For the purposes of the invention, it is preferably understood that the said pathogen insects belong to the Lepidoptera kind, among which we could mention plague species *Tuta absoluta, Proeulia* spp., *Spodoptera frugiperda, Plutella xylostel, Agrotis* spp., *Lobesia botrana*.

The following are examples of preferred realization for this invention, which provide information on some of the possible realization forms for the application of this invention formula in the treatment and control of some agricultural plagues. These examples represent preferred modes, with no limitation for the rest of possible agricultural applications that an average technical expert could design.

EXAMPLES

Example 1 a) Formula with Strain *Bacillus thuringiensis* var. Kurstaki NRRL B-50551 (BI with One Strain)

Preparation of the pesticide formula: a formula was prepared that includes bacteria material from strain *Bacillus thuringiensis* var. kurstaki NRRL B-50551 in the form of dry powder with $10^8$ UFC/g concentration.

b) Formula with Strain *Bacillus thuringiensis* var. Kurstaki NRRL B-50552 (BI with One Strain)

Preparation of the pesticide formula: a formula was prepared that includes bacteria material from strain *Bacillus thuringiensis* var. kurstaki NRRL B-50552 in the form of dry powder with $10^8$ UFC/g concentration.

c) Formula with Strain *Bacillus thuringiensis* var. Kurstaki NRRL B-50553 (BI with One Strain)

Preparation of the pesticide formula: a formula was prepared that includes bacteria material from strain *Bacillus thuringiensis* var. kurstaki NRRL B-50553 in the form of dry powder with $10^8$ UFC/g concentration.

Example 2

In Vitro Assay to Assess the Effect of the Invention Formulae Applying Three Individual Strains on the *Agrotis* spp Plague Mortality.

The assay was carried out by placing *Agrotis* larvae in their second development stage on previously selected tomato leaves. First, treatments were applied with suspensions containing different individual strains of *Bacillus thuringiensis*, NRRL B-50551, NRRL B-50552, and NRRL B-50553 at a dose of 1 g/liter, using a formula with $1\times10^8$ UFC/g concentration. After the treatment application, leaves were left to dry in order to place the previously selected larvae, which were kept in a growth chamber during 144 hours, in a regime of 12-hour light during the night before being placed on the samples treated. Mortality was assessed very 24 hours. For each treatment, the assay was repeated 15 times, each time using 10 larvae. A comparative assay of the effect was carried out using a treatment with commercial pesticide Dipel WG (which includes *Bacillus thuringiensis* 6.4% p/p). Data were adjusted according to the control mortality.

Controls: (a group of samples with no treatment whatsoever were submitted to the effect of larvae and mortality was assessed).

TABLE 1

*Agrotis* mortality from the effect of DIPEL, expressed in percentages and at different times at a dose of 40 ug/ml.

| Strain | hours | | | | | |
|---|---|---|---|---|---|---|
| | 24 | 48 | 72 | 96 | 120 | 144 |
| Control | 0.0% e* | 0.0% e | 5% d | 7% d | 9% d | 12% d |
| Dipel WG (*Bacillus thuringiensis* 6.4% p/p) | 8.3% d | 26.7% c | 48.3% c | 57.8% b | 87.7% ab | 92.6% a |
| *Bacillus thuringiensis* var. *kurstaki* NRRL B-50551 | 90.0% a | 90.0% a | 90.0% a | 90.0% a | 90.0% a | 90.0% a |
| *Bacillus thuringiensis* var. *kurstaki* NRRL B-50552 | 0.0% e | 0.0% e | 0.0% e | 84.0% ab | 87.0% a | 90.0% a |
| *Bacillus thuringiensis* var. *kurstaki* NRRL B-50553 | 0.0% e | 0.0% e | 20.0% | 65.0% b | 90.0% a | 90.0% a |

*Same letters indicate the absence of Tukey HSD >0.05 significant differences.

According to the results in table 1, it is possible to note that the three strains, individually, reached mortality levels similar to DIPEL after 144 hours; however, it is also noted that strains under study reached control levels statistically higher than Dipel after 96 hours, with strain NRRL B-50551 outstanding and reaching mortality levels of 90% after 24 hours. This assay shows the superior effect of this invention strains compared to the commercial reference, Dipel.

Example 3

Use of BI for *Proeulia* spp. Control, Compared to the Use of Pesticide (DIPEL®)

This assay was carried out in a location in Totihue, 6th Region, Chile, in a Merlot vineyard, and application was started from the fruit setting to the harvest.

Treatments:
T1. Orchard management (Dipel WG (*Bacillus thuringiensis* 6.4% p/p)): two applications during the season.
T2. BI application during blooming, veraison and before leaf falls, against damage (5 g/l).

Water volume was that normally used in the estate, according to the phenologic condition (around 1000 liters/ha).

Applications were carried out with turbo-nebulizer, where all nozzles were kept open.

The assay surface corresponded to one hectare per treatment, equal to one block per treatment, separated by a road.

The variety used in the assay was Merlot vines.

Experimental Design

An experimental random design was used, with two treatments and four repetitions per treatment, with the application of BI and using the orchard management as control.

Assessments

As a confirmation parameter, fruit damage was assessed (bunches of grapes): number of damaged bunches/number of bunches damaged by *Proeulia* during the season.

Assessments were carried out from the fruit setting to harvest, when four rows per block were assessed (with treatment and control) of 30 plants per row, i.e. one hundred a sixty plants approximately. Each clearing corresponded to approximately 6 linear meters.

Results

As shown in the diagram in FIG. 1, the percentage of grape bunches damaged by *Proeulia* during treatment with BI was significantly less than with application of the commercial reference (T1); this was less than half in the treatment with BI ($p<0.05$), compared to the control.

These results allow concluding, although 4 applications were carried out and there is still the winter application to be carried out, that BI is effective in *Proeulia* control, decreasing damage associated to this plague in wine grapes when compared to the orchard management (commercial reference).

This way, BI results an effective alternative for the control of this plague in wine grapes, especially for organic vineyards, considering the optimistic results of this assay.

Example 4

Assessment of the Insecticide Capacity of Three BI Strains in Tomato Cultivation for the Control of Plague *Tata absoluta*.

This assay assesses the effect of the application of a formula according to the invention, which includes the three *Bacillus thuringiensis* strains (BI) in order to calculate the level of damage caused by tomato moth (*Tuta absoluta*) on tomatoes under organic handling and greenhouse conditions.

Methodology

The assay was carried out in a greenhouse under organic management at Panguilemo Experimental Station belonging to Universidad de Talca (7th Region, Chile). Tomato plants of the *Maria Italia* variety were used in their fourth flower development stage. As control, an equivalent greenhouse was assessed, to which the formula not containing the invention *Bacillus* strains was applied.

The formula used contained the three strains of *Bacillus thuringiensis* NRRL B-50551, NRRL B-50552, and NRRL B-50553 which, in laboratory controlled assays, individually and combined, showed insecticide effectiveness higher than that of the commercial strain *Bacillus thuringiensis* var. kurstaki (Dipel WG (*Bacillus thuringiensis* 6.4% p/p)) on tomato moth.

Design and Statistical Analysis:

Completely randomized design with five repetitions of ten plants each. Statistical analysis was carried out with one-way ANDEVA. After finding a significant effect of treatments, a multiple comparison of significant minimum difference was carried out in order to separate means (LSD). Data was submitted to the Kolmogorov-Smirnov and Barlett tests and, in the cases where assumptions necessary for ANDEVA were not met, they were adjusted according to the Box-Cox test (damage area and severity).

Treatments

T0: Control with no applications

T1: Comparative application with Dipel WG (*Bacillus thuringiensis* 6.4% P/P)

T6: BI $10^8$ UFC/g BI application in a dose of 1.5 g/l

Both treatment doses were 1 g/l for their combination.

Treatments were applied once with SOLO® backpack sprayer of 20 liter capacity using an application volume equivalent to 300 l/ha. Treatment application was carried out based on monitoring with pheromone trap (*Tuta* Stop) and plant damage monitoring; the application threshold was 50 individuals/traps/day with 6% of eggs, larvae, or visually observed damage. In this assay, 50 plants were used, taken at random from the assay plants, after which we waited for the accumulation of degree-days (103.2). This condition occurred in the summer and assessments were carried out seven days after the application. This allowed the formula acting on larvae in the first and second stage.

Assessments:

The effect of treatments was assessed by measuring the damaged area ($cm^2$) of leaflets and larva mortality, as well as the number of dead larvae in 10 real leaves per plant.

Results

TABLE 2

Effect of different tomato moth strains on the damage and mortality.

| Treatment | Damaged area ($cm^2$/leaflet) | Mortality (dead larvaes/ 10 real leaves/plants) |
|---|---|---|
| T0: Control | 9.167 a* | 0.667 a |
| T1 Dipel WG (*Bacillus thuringiensis* 6.4% p/p) | 5.383 a | 2.00 b |
| T2 (BI, mix of 3 strains) | 14.667 b | 1.667 b |

*Same letter: there is no significant statistics difference (LSD) P < 0.05.

Table 2 shows the average of each treatment for each parameter assessed. As it may be noted, for the parameter assessed, corresponding to the damaged area, the best treatment is achieved with the BI inventive formula, which contains the three strains and results in a less damaged area compared to the commercial reference Dipel WG (*Bacillus thuringiensis* 6.4% p/p). With regard to mortality, both treatments reached mortality levels higher than those of the control treatment.

Conclusions

Based on the data obtained from this BI invention formula, corresponding to the treatment that includes three strains, it is possible to control the *Tuta absoluta* plague in tomatoes grown in a greenhouse with organic management.

Example 5

In Vitro *Tuta absoluta* Mortality Assay with BI Insecticide (with One, Two, or Three Strains).

In this assay, *Tuta absoluta* larvae in their second development stage were placed on tomato leaves previously treated with a suspension containing different strains of *Bacillus thuringiensis* (NRRL B-50551, NRRL B-50552, and NRRL B-50553) at a dose of 1 g/liter, using a formula with a concentration of $1\times10^8$ UFC/g. After the treatment, leaves were left to dry and larvae were placed on them later; leaves with larvae were kept in a growth chamber for 144 hours, under a regime of 16 hours of light and 8 hours of darkness. Larvae mortality was assessed every 24 hours. Each treatment included 15 repetitions, each one of them with a set of 10 larvae. Data were adjusted according to the control mortality.

Methodology

The assay was carried out during the 2005-2006 season at a location in Quillota. Applications were carried out on Cv Fortaleza tomato plants, with a first bunch formed and second blooming. Applications were carried out with a nozzle at 2.5 bar pressure, using an application volume equivalent to 200 l/ha. Application dates were based on the orchard standard monitoring protocol; application dates were October 10, 17, and 24. Assessments were carried out on October 29 to verify the presence of live larvae and leaflet damage, while the number of bunches assessment was carried out during the harvest (February 2006).

Statistical Design:

The experimental design included three repetitions per treatment and two aisles per repetition, where 30 plants were assessed in each of them. The statistical analysis was carried out with one-way ANDEVA, with the assessed products as main effect. After finding the treatments significant effect, a multiple comparison of significant minimum difference was carried out in order to separate averages (LSD). Data were submitted to Kolmogorov-Smirnov and Barlett tests and, in cases where the assumptions necessary for ANDEVA were not met, they were adjusted according to the Box-Cox test (leaflet damage).

TABLE 3

*Agrotis* mortality by DIPEL effect (40 mg/ml) expressed in percentages at different times.

| | hours | | | | | |
|---|---|---|---|---|---|---|
| Strain | 24 | 48 | 72 | 96 | 120 | 144 |
| Control | 0.0% f | 0.0% f | 0% f | 7% e | 9% e | 12% de |
| Dipel | 8.3% e | 26.7% d | 48.3% c | 57.8% c | 87.7% ab | 92.6% a |
| Bt strain NRRL B-50551 | 80.0% b | 80.0% b | 85.0% ab | 90.0% a | 90.0% a | 90.0% a |
| Bt strain NRRL B-50552 | 0.0% e | 0.0% e | 0.0% e | 84.0% ab | 87.0% ab | 90.0% ab |
| Bt strain NRRL B-50553 | 0.0% e | 0.0% e | 20.0% | 65.0% c | 90.0% ab | 90.0% ab |
| NRRL B-50551 + NRRL B-50552 | 80.0% b | 80.0% b | 90.0% ab | 90.0% a | 90.0% ab | 90.0% ab |
| NRRL B-50552 + NRRL B-50553 | 0.0% e | 0.0% e | 20.0% | 65.0% b | 90.0% ab | 90.0% a |
| NRRL B-50551 + NRRL B-50553 | 90.0% ab | 93.0% ab | 94.0% a | 94.0% a | 94.0% a | 95.0% a |
| NRRL B-50551 + NRRL B-50552 + NRRL B-50553 | 90.0% ab | 95.0% ab | 95.0% ab | 96.0% a | 100.0% a | 100.0% a |

Based on the results in table 3, it is possible to note that the three strains reach mortality levels similar to the commercial reference used, DIPEL, after 144 hours, for formulae containing individual or combined strains, with only two of them or containing the three strains. However, the strains under study reach control levels statistically higher than Dipel after 96 hours, even strain N1 reaches 90% mortality levels after 24 hours, showing a higher effect than that of the commercial reference given by Dipel. When analyzing the mixtures, it is noted that strain N2 and N3 increase their action when combined with N1, which also increases its actions when combined with the two previous strains.

Example 6

Assessment of BI (with Three Strains) for the Control of Tomato Moth Compared to Treatment with a Chemicals Product Purpose:

This assay assesses the application of a combined formula containing the three *Bacillus thuringiensis* strains, NRRL B-50551, NRRL B-50552, and NRRL B-50553, (T2=BI with three strains) in order to calculate the level of damage caused by the tomato moth under greenhouse conditions in comparison to a commercial product of chemicals origin.

Treatments

T1: Orchard management (Karate 5 EC, active substance lambda-cyhalothrin) 25 ml/100 l T2: BI with 3 strains ($10^8$ ufc/g) in a dose of 2 g/l Assessments Although no differences were noted with regard to the number of damaged leaflets per plant (diagram in FIG. 5), a reduced number of live larvae per plant was noted (diagram in FIG. 6); this may be because BI does not show an immediate effect on larvae, allowing them to generate damage in leaflets before they die, for which reason no live larvae were noted on the plants. However, live larvae were noted among plants under chemical treatment, with a contact effect.

Results

In the biologic treatment, a significantly higher performance was noted in the treatment with BI compared to the chemical one, which would be mainly due to the fact that plants with the biologic treatment with not present damage in their growth apex, which allowed them a significantly higher number of bunches per plant (diagram in FIG. 7).

Conclusions

Based on the data gathered, the BI product shows control over *Tuta absoluta* in tomatoes grown in greenhouses under conventional management with the dose, wetting volume, and periodicity indicated in this assay.

Example 7

Assessment of BI (Three Strains) for *Agrotis* spp Control on Maize
Purpose:
Assessing applications of the invention BI formula, which includes the three *Bacillus thuringiensis* strains (BI), NRRL B-50551, NRRL B-50552, and NRRL B-50553, in order to calculate the level of damage caused by cutworms on maize (*Agrotis* spp.) under controlled conditions.
Methodology
Maize was planted in 25×20 cm black plastic bags, in a substrate formed by compost, peat, and perlite in a 1:1:0.5 ratio. Plants were kept in the laboratory, in day light, in a regime of 12 hours light at 25° C. (with lights on) and a minimum temperature of 16° C. (with lights off).
Larvae (100) were supplied by Universidad de Talca Laboratorio de Sanidad Vegetal. In order to perform both tests, it was necessary to create a system for the plant to continue developing and the larva be fed only from the plant to which it had been inoculated. The following image shows the system that met the said requirements.
The system is formed by two 1-liter transparent plastic glasses joined together with tape in an opposite way. The base of the glass in contact with the soil was cut and the glass was buried in the substrate approximately 1 cm. A 3×3 cm window was cut in the glass on top in order to release the plant evapotranspiration. In addition, the base of this glass was perforated with a hot pin for the same purpose.
This way, we ensured that the larva would feed only from the inoculated plant. In this assay, the following products were used: *Bacillus thuringiensis* and Engeo® (Thiametoxam+Lambdacihalotrina) and an absolute control.

TABLE 4

| Treatment | Product | Dose |
|---|---|---|
| T1 | Absolute control (sterile distilled water) | — |
| T2 | BI | 3 g/L |
| T5 | Engeo ® | 1 ml/L |

Total design was completely at random, with three repetitions per treatment (3), with a plant as experimental unit.

Controllers were applied 48 hours before the larvae inoculation to the plant. One larva per plant was applied, and they were assessed every 24 hours.
Assessment of Larva Mortality
Clearly, the chemical insecticide has a higher mortality level, reaching 100%, while the biologic insecticide reached around 40% mortality, being statistically different from the chemical control, as well as from absolute control, becoming a viable control alternative, especially in systems where the use of chemical insecticides is restricted or prohibited.

Example 8

Assessment of the BI Concentrations (with Three Strains) on Different Agricultural Plagues In Vitro.
In this test, second stage larvae, obtained from eggs of each one of the species, were placed on leaves whose surface had been sterilized and then immersed for 5 minutes in the different treatments for tomato in the case of *Tuta absoluta*, grape in the case of *Agrotis* and *Proeulia*, bean in the case of *Spodoptera*, and cabbage in the case of *Plutella*, all of them placed on previously sterilized 5 cm petri plates. Larvae were placed on these leaves inside the plates and kept for 72 hours in a culture chamber at 25° C., with 16 hours day/8 hours night regime; after this period, each species mortality level at each dose was assessed.
Treatments consisted in controls with the BI formula with three strains, and in increasing concentrations, from 10 spores/g to $10^{11}$ spores per g, with the addition of 1.5 g of each concentration to 1 liter water, where each species leaves were immersed.
Each treatment was repeated 10 times, with 10 plates each, with a larva of each species.
Design was a 12×5 factorial arrangement, where factors were doses and larva species.
Results
The dose factor, as well as the larva species factor, showed significant effects. From $10^3$ concentration, significant differences were noted in control without the IB formula with three strains; from $10^8$ UFC/g concentration no significant mortality increases were noted, being *Tuta absoluta*, *Agrotis* spp and *Proeulia* larvae the most susceptible ones, while *Spodoptea* and *Plutella* showed mortality levels significantly lower than the former.
Mortality (%) of different second stage larva species in front of different bacteria insecticide (BI) formula concentrations under in vitro conditions 72 hours after the treatments application. Values followed by the same letter indicate the absence of significant Tukey HSD differences.

TABLE 5

| | doses (spores') | | | | | | | | | | | |
|---|---|---|---|---|---|---|---|---|---|---|---|---|
| Insects | 0 | 10 | 100 | $10^3$ | $10^4$ | $10^5$ | $10^6$ | $10^7$ | $10^8$ | $10^9$ | $10^{10}$ | $10^{11}$ |
| *Tuta absoluta* | 0 h* | 0 h | 3 h | 14 fg | 36 de | 50 d | 64 c | 87 b | 90 a | 92 ab | 93 a | 95 ab |
| *Agrotis* spp | 0 h | 0 h | 5 h | 21 f | 41 de | 46 d | 59 c | 83 b | 90 ab | 90 ab | 91 ab | 94 ab |
| *Proeulia* spp | 0 h | 0 h | 2 h | 27 f | 35 e | 48 d | 74 bc | 82 b | 94 a | 95 a | 95 a | 98 a |
| *Spodoptera frugiperda* | 0 h | 0 h | 6 h | 12 g | 30 e | 39 e | 71 bc | 78 bc | 87 b | 86 b | 87 b | 87 b |
| *Plutella xylosteal* | 0 h | 0 h | 0 h | 13 g | 21 | 34 e | 54 | 65 c | 83 b | 84 b | 84 b | 86 b |

*Equal letters indicate the absence of significant Tukey Hsd p < 0.05 differences.

Example 9

Effectiveness of BI Formula with Three Strains in the Control of Grape Berry Moth (*Lobesia botrana*) Under Laboratory Conditions and at Different Concentrations This assay assessed the effectiveness of the BI invention formula with three strains, NRRL B-50551, NRRL B-50552, and NRRL B-50553 under controlled laboratory conditions, in connection with grape berry moth (*Lobesia botrana*) control in three concentrations, compared to the standard micro-biologic insecticide Dipel (*B. thuringiensis* var. kurstaki strain HD-1).

The assay was carried out at the Universidad de Talca Laboratorio de Sanidad Vegetal using *Lobesia botrana* larvae provided by SAG (Servicio Agricola y Ganadero) and following the quarantine regulations of the said institution. As experimental unit, parts of set grape bunches were used, inside plastic containers covered by a mesh. Pieces of bunches were selected weighting around 5 g and formed by recently set grapes and their corresponding rachis. Wine grape bunches were used (Cabernet Sauvignon). No insecticide was previously applied to these bunches. Each repetition was formed by a group of ten experimental units. Five repetitions were carried out for each treatment. In total, 250 larvae were used for the entire assay.

TABLE 6

Products and doses assessed for the control of grape berry moth (*Lobesia botrana*) on grape bunches under laboratory conditions.

| Treatment | Products | I.A. | Dose (g HL$^{-1}$) |
|---|---|---|---|
| 1. | CONTROL | — | — |
| 2. | BI (3 strains) | *Bacillus thuringiensis* var. *kurstaki* | 100 |
| 3. | BI (3 strains) | *Bacillus thuringiensis* var. *kurstaki* | 200 |
| 4. | BI (3 strains) | *Bacillus thuringiensis* var. *kurstaki* | 300 |

Products used in the assay (table 6) were dissolved in distilled water and applied by immersing the bunches. After draining and drying residues from the product application, a second-third stage larva was placed on each experimental unity and kept under controlled temperature (20±1° C.) until 85% pupation was completed in the control treatment. During this period, the number of dead larvae was assessed and the presence of feeding signs was recorded (presence of fecal matter) on the 3$^{rd}$, 6$^{th}$, 8$^{th}$, and 11$^{th}$ day after application (DDA). Later, adult mortality was assessed to this status, considering that dead pupas that did not emerge until 45 DDA. Dead adults were kept at 60° C. for 48 hours in order to calculate their dry weight. Finally, a variance analysis (Andeva) was carried out of measures repeated in time with larvae mortality transformed in an angular way. Mortality in adult state and dry weight were analyzed with Andeva of a factor with adult mortality transformed in an angular way and dry weight without transformation. When Andeva found significant differences between treatments (P<0.05), averages were separated according to Duncan multiple comparison test.

Results and Discussion

Treatment with BI formula with 3 strains in its higher dose of 300 gHL$^{-1}$ presented significantly higher mortality that the control treatment from the first to the last assessment (table 7). Mortality in these two same treatments did not present significant differences in any of the assessments (table 7). Treatment with BI formula with 3 strains in its intermediate dose of 200 gHL$^{-1}$ presented higher mortality that the control treatment from 3 DDA to 11 DDA, with no significant differences with the standard in any of the assessments (table 7). The lowest BI formula with 3 strains assessed showed no significant difference with the control treatment, and presented less mortality than the standard treatment in a permanent way (table 7). In the case of survival to adult status, doses of 200 and 300 $gHL^{-1}$ Betk-03 presented mortality significantly higher than those of the control treatment (table 7).

TABLE 7

Grape berry moth (*Lobesia botrana*) mortality at different moments from the application of treatments on grape bunches under laboratory conditions.

| Products | 3 DDA | 6 DDA | 8 DDA | 11 DDA | Adult |
|---|---|---|---|---|---|
| CONTROL | 2.5 a* | 2.5 a | 5.0 a | 7.5 a | 17.5 a |
| BI (3 strains) (100 $gHL^{-1}$) | 10.0 ab | 17.5 ab | 25.0 ab | 30.0 ab | 47.5 b |
| BI (3 strains) (200 $gHL^{-1}$) | 7.5 ab | 15.0 ab | 37.5 bc | 42.5 bc | 60.0 bc |
| BI (3 strains) (300 $gHL^{-1}$) | 12.5 ab | 50.0 b | 62.5 bc | 65.0 bc | 72.5 c |

*Same letters indicate the absence of significant Tukey Hsd $p < 0.05$ differences.

Dry weight or survivor adults from all treatments assessed did not show significant differences with the control treatment (table 8).

TABLE 8

Dry weight of grape berry moth (*Lobesia botrana*) adults surviving different treatments under laboratory conditions.

| Products | Adults dry weight (g) |
|---|---|
| CONTROL | 0.00075 |
| BI (3 strains) (100 $gHL^{-1}$) | 0.00068 |
| BI (3 strains) (200 $gHL^{-1}$) | 0.00078 |
| BI (3 strains) (300 $gHL^{-1}$) | 0.00073 |

Results obtained under laboratory conditions indicate that BI micro-biologic insecticide formula (3 strains) in doses of 200-300 $gHL^{-1}$ presents an effective control of first generation grape berry moth larvae. Larvae mortality levels reached by the 200-300 $gHL^{-1}$ dose of BI formula (3 strains) are comparable to those reported in literature on field assays carried out in different countries in Europe (Ifoulis & Savopoulou-Soultani, 2004, Ruiz de Escudero et al., 2007; Shahini et al., 2010). Also, BI formula (3 strains) in 100-300 $gHL^{-1}$ doses causes a significant reduction of adults emergency, although dry weight of individuals completing their development are equal to those in the standard and control treatments. This would indicate that possible sub lethal effects would not affect the surviving adults' reproductive capacity. Under plague low incidence conditions, it is possible to apply the lower dose of 100 $gHL^{-1}$ of the BI formula (3 strains) in order to reach a significant reduction of emergency in adults in connection with the control, as under higher infestation conditions it is necessary to apply doses of 200-300 $gHL^{-1}$ Betk-03.

CONCLUSIONS

1. BI insecticide formula (3 strains) applied in 200-300 $gHL^{-1}$concentrations present grape berry moth larvae (*Lobesia botrana*) control levels significantly higher than those of the control treatment, with no significant differences with the assessed standard treatment; therefore, it effectively controls this plague on grape under laboratory conditions, and it is recommended for use in the field under medium and high infestation conditions.

2. BI insecticide formula (3 strains) applied in 100 gHL$^{-1}$ concentrations presents adult emergency reduction levels in grape berry moth (*Lobesia botrana*) significantly higher than that of the control treatment; therefore, it effectively controls this plague on grape under laboratory conditions, and it is recommended for use in the field under low infestation conditions.

3. No phyto-toxicity symptom on grape bunches treated with the BI insecticide formula (3 strains) was noted.

The invention claimed is:

1. A composition for biologic control of insect pathogens of plants wherein said composition is free of conventional insecticides and comprises three *Bacillus thuringiensis* variety (var.) kurstaki strains deposited with the Agricultural Research Service Culture Collection (ARS) with accession numbers NRRL B-50551, NRRL B-50552, and NRRL B-50553 or endotoxins derived from said three strains.

2. A composition according to claim 1, wherein the composition comprises crystals of endotoxins derived from said strains.

3. The composition according to claim 1, wherein the composition form is selected from the group consisting of a suspension capsule for seed treatment; a bait in any of its forms; a combo pack in any of its forms, such as concentrates, emulsifiable, concentrate, encapsulated, or miscible suspension of ultra-low volume; tablets in any of their forms, of ultralow volume; oil-in-water and water-in-oil emulsions in the form of gel, concentrate paste, or emulsifiable gel; dispersible, encapsulated, fine, soluble, emulsifiable granules; macro granules or micro granules; paste; contact, wettable or dispersible powder; a solution; and a concentrate suspension.

4. The composition according to claim 1, wherein the strains are added to the composition at concentrations between $10^2$ UFC/g and $10^{12}$ UFC/g UU of each strain.

5. The composition of claim 1, further comprising zeolite as a carrier.

6. A method for protecting a plant from an insect pathogen, the method comprising applying a composition according to claim 1 to the plant, a part of the plant, soil adjacent to the plant, or an area surrounding the plant.

7. A method according to claim 6, wherein the composition is applied to a part of the plant selected from a flower, a fruit, a seed, a leaf, a stem, a root, and/or a rhizome.

8. A method according to claim 6, wherein the method protects the plant from a pathogen insect from the order Lepidoptera.

9. A method according to claim 8, wherein said pathogen insect from the order Lepidoptera is selected from the group consisting of species *Tuta absoluta, Proeulia* spp., *Spodoptera frugiperda, Plutella xylostella, Agrotis* spp., and *Lobesia botrana*.

10. A method for the protection of a plant from an insect pathogen, the method comprising applying a composition according to claim 1 to the plant, a part of the plant, soil adjacent to the plant, or an area surrounding the plant, wherein the composition comprises crystals of endotoxins derived from said three strains.

11. A method according to claim 10, wherein the composition is applied to a part of the plant selected from a flower, a fruit, a seed, a leaf, a stem, a root, and/or a rhizome.

12. A method according to claim 10, wherein the strains are added to the composition at concentrations between $10^2$ UFC/g and $10^{12}$ UFC/g UU of each strain.

13. A method according to claim 10 wherein the composition protects the plant from a pathogen insect from the order Lepidoptera.

14. A method according to claim 13, wherein said pathogen insect from the order Lepidoptera is selected from the group consisting of species *Tuta absoluta, Proeulia* spp., *Spodoptera frugiperda, Plutella xylostella, Agrotis* spp., and *Lobesia botrana*.

* * * * *